US 6,649,765 B1

(12) United States Patent
Vidyadhar et al.

(10) Patent No.: US 6,649,765 B1
(45) Date of Patent: Nov. 18, 2003

(54) PROCESS FOR THE PREPARATION OF 1-BENZYL-4(5,6-DIMETHOXY-1-INDANON)-2-YL) METHYL PIPERIDINE HYDROCHLORIDE (DONEPEZIL HCL)

(75) Inventors: Joshi Shreerang Vidyadhar, Maharashtra (IN); Naidu Avinash Venkatraman, Maharashtra (IN); Sutar Rajiv Pandurang, Maharashtra (IN)

(73) Assignee: USV Limited, BSD MARG., Maharashtra (IN)

( * ) Notice: Subject to any disclaimer, the term of this patent is extended or adjusted under 35 U.S.C. 154(b) by 0 days.

(21) Appl. No.: 10/365,717

(22) Filed: Feb. 12, 2003

(51) Int. Cl.⁷ .................... C07D 211/02; C07D 211/08
(52) U.S. Cl. ........................... 546/185; 546/206
(58) Field of Search .................. 546/185, 206

(56) References Cited

U.S. PATENT DOCUMENTS

| 4,895,841 A | 1/1990 | Sugimoto et al. |
| 5,606,064 A | 2/1997 | Lensky |
| 6,252,081 B1 | 6/2001 | Iimura |

FOREIGN PATENT DOCUMENTS

| WO | WO 97/22584 | 6/1997 |

*Primary Examiner*—Charanjit S Aulakh
(74) *Attorney, Agent, or Firm*—Knobbe Martens Olson & Bear LLP

(57) ABSTRACT

A process for the preparation of 1-benzyl-4-[(5,6-dimethoxy-1-indanon)-2-yl]methylpiperidine hydrochloride (Donepezil HCl). 5,6-Dimethoxy-2-(pyridin-4-yl)methylene inda-1-one is hydrogenated with a noble metal oxide catalyst in an organic solvent at 20–50° C. and 10–45 psi gauge pressure. The resulting 4-[(5,6-dimethoxy-1-indanon)-2-yl] methyl piperidine is alkylated with an alkylating agent in an organic solvent at 30–80° C.

7 Claims, No Drawings

PROCESS FOR THE PREPARATION OF 1-BENZYL-4(5,6-DIMETHOXY-1-INDANON)-2-YL) METHYL PIPERIDINE HYDROCHLORIDE (DONEPEZIL HCL)

FIELD OF INVENTION

This invention relates to a process for the preparation of 1-benzyl-4-[(5,6-dimethoxy-1-indanon)-2-yl]methyl piperidine hydrochloride (Donepezil HCl) of the formula 1.

Formula I

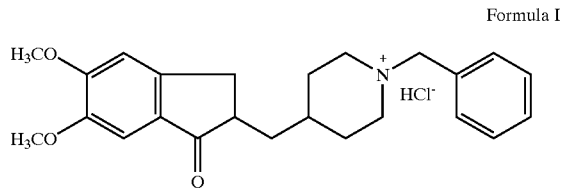

Compound of the formula 1 commonly known as Donepezil HCl is used for treatment of Central Nerve System (CNS) disorders.

PRIOR ART

U.S. Pat. No. 4,895,841 describes preparation of Donepezil HCl by reacting 5,6-dimethoxy-1-indanone with 1-benzyl-4-formylpiperidine in the presence of a strong base such as lithium diisopropyl amide followed by reduction with palladium carbon catalyst (Examples 3 and 4). Overall yield of Donepezil HCl is reported to be 50.8% (62%×82%).

U.S. Pat. No. 5,606,064 teaches the preparation of Donepezil HCl by the reaction of 5,6-dimethoxy-1-indanone with pyrindin-4-aldehyde. The resulting 5,6-dimethoxy-2-(pyridin-4-yl)methyleneinda-1-one is reacted with benzyl bromide to afford 1-benzyl-4-[(5,6-dimethoxy-1-indanon-2-ylidine]methyl pyridinium bromide which on reduction with platinum oxide catalyst afforded Donepezil HCl. (Examples 2, 4 and 6). Overall yield of Donepezil HCl 58.5% (87%×83%×81%).

PCT Publication No WO 97/22584 reports preparation of Donepezil HCl by reacting pyridine-4-aldehyde with malonic acid. The resulting 3-(pyridin-4-yl)-2-propenoic acid was reduced with rodium on carbon under hydrogen atmosphere to give 3-(piperidin-4-yl)-2-propionic acid which on reaction with methyl chlorocarbonate gave 3-[N-(methoxycarbonyl)piperidin-4-yl]propionic acid. On reacting 3-[N-(methoxycarbonyl)piperidin-4-yl]propionic acid with oxalyl chloride, methyl 4-(2-chlorocarbonylethyl) piperidin-1-carboxylate is obtained which on reaction with 1,2-dimethoxy benzene in the presence of aluminium chloride afforded 4-[3-(3,4-dimethoxyphenyl)-3-oxopropyl] piperidin-1-carboxylate. On reacting 4-[3-(3,4-dimethoxyphenyl)-3-oxopropyl]piperidin-1-carboxylate with tetramethyl diamino methane, 4-[2-(3,4-dimethoxy benzoyl)allyl]piperidin-1-carboxylate is obtained which on treatment with sulphuric acid gave methyl 4-(5,6-dimethoxy-1-indanon-2-yl methyl)piperidin-1-carboxylate. On decarboxylating 4-(5,6-dimethoxy-1-indanon-2-yl methyl)piperidin-1-carboxylate, 5,6-dimethoxy-2-(piperidin-4-yl methyl)-1-indanone is obtained which on treatment with benzyl bromide afforded Donepezil HCl (Example 1 to 6). Overall yield of Donepezil HCl 19.3% (70%×84%×100%×68%×79%×61%).

U.S. Pat. No. 6,252,081 teaches the preparation of Donepezil HCl by the reaction of 1-indanone derivative with carbonate ester. The resulting 2-alkoxycarbonyl-1-indanone derivative is halogenated with (4-pyridyl)methyl or a salt thereof and decarboxylated successively to give 2-(4-pyridyl)methyl-1-indanone derivative. On reacting the 2-(4-pyridyl)methyl-1-indanone derivative with benzyl bromide, their quarternary ammonium salts are formed, which on reduction with platinum oxide catalyst gives Donepezil HCl (Examples 1 to 3). Overall yield of Donepezil HCl 82% (98%×85%×100%×99%).

The prior art processes employs 1-benzyl-4-formyl piperidine as starting material whose synthesis is low yielding and involves use of lithium diisopropyl amide. The reaction of 1-benzyl-4-formyl piperidine with 5,6-dimethoxy-1-indanone also involves use of lithium diisopropyl amide and cryogenic temperatures which are expensive and are not economically viable. Lithium diisopropyl amide is toxic and needs to be carefully handled. Many a time selective reduction of double bond to yield 1-benzyl-4-[(5,6-dimethoxy-1-indanon)-2-yl]methyl piperidine hydrochloride is difficult to achieve. Besides, the selective reduction of double bond to give 1-benzyl-4-[(5,6-dimethoxy-1-indanon)-2-yl]methyl piperidine hydrochloride is many a time coupled with formation of side products which are difficult to separate. Yield of the product is also affected due to the formation of the side products. Use of oxalyl chloride chemistry is difficult for scale up. Besides the oxalyl reaction also involves many protection deprotection chemistry and the over all yield is very low. Raw materials like methyl chlorocarbonate or tetramethyl diaminomethyl are expensive and difficult to source commercially. The prior art processes are also time consuming and difficult to carry out as they involve many steps.

OBJECTS OF INVENTION

An object of the invention is to provide a process for the preparation of 1-benzyl-4-[(5,6-dimethoxy-1-indanon)-2-yl]methyl piperidine hydrochloride which eliminates formation of byproducts and gives high yield of the product and is efficient and economical.

Another object of the invention is to provide a process for the preparation of 1-benzyl-4-[(5,6-dimethoxy-1-indanon)-2-yl]methyl piperidine hydrochloride which employs less number of reaction steps and is less time consuming and easy and convenient to carry out.

Another object of the invention is to provide a process for the preparation of 1-benzyl-4-[(5,6-dimethoxy-1-indanon)-2-yl]methyl piperidine hydrochloride which eliminates use of hazardous reagents and is safe to carryout.

Another object of the invention is to provide a process for the preparation of 1-benzyl-4-[(5,6-dimethoxy-1-indanon)-2-yl]methyl piperidine hydrochloride which employs cheaper and easily available raw materials.

Another object of the invention is to provide a process for the preparation of 1-benzyl-4-[(5,6-dimethoxy-1-indanon)-2-yl]methyl piperidine hydrochloride which is suitable for industrial scale up.

DETAILED DESCRIPTION OF INVENTION

According to the invention there is provided a process for the preparation of 1-benzyl-4-[(5,6-dimethoxy-1-indanon)-2-yl]methylpiperidine hydrochloride (Donepezil HCl) of the formula I

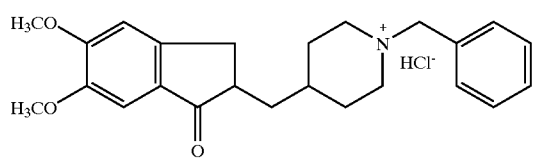

Formula I comprising hydrogenating 5,6-Dimethoxy-2-(pyridin-4-yl) methylene inda-1-one with a noble metal oxide catalyst in an organic solvent at 20–50° C. and 10–45 psi gauge pressure to form 4-[(5,6-dimethoxy-1-indanon)-2-yl]methyl piperidine of the formula II

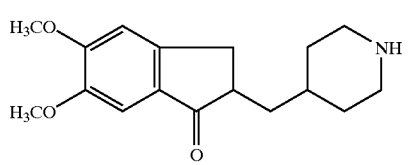

Formula II which is alkylated with an alkylating agent in an organic solvent at 20–80° C.

The organic solvent used in the hydrogenation of compound of the formula II may be tetrahydrofuran, methanol or acetic acid or combination thereof preferably acetic acid-:methanol mixture.

The noble metal oxide catalyst used in hydrogenation may be platinum or palladium oxide, preferably platinum oxide.

Preferably hydrogenation is caried out at 25–40° C. and 25–40 psi gauge

The alkylating agent may be benzyl bromide or benzyl chloride, preferably benzyl bromide.

The organic solvent used in the alkylation reaction may be methylenedichloride, triethyl amine or mixtures thereof preferably methylenedichloride and triethyl amine mixture.

Preferably the alkylation is carried out at 30–40° C.

The process of the invention eliminates formation of byproducts and gives high yield of the product (about 92%). It employs cheaper and easily available raw materials and eliminates use of hazardous reagents. It is, therefore, efficient and economical and safe to carryout. It comprises only two steps and is, therefore, less time consuming and is easy and convenient to carryout. For the above reasons, it is also suitable for industrial scale up.

The following examples are illustrative of the invention but not limitative of the scope thereof.

EXAMPLE 1

4-[5,6-dimethoxy-1-indanon)-2-yl]methyl piperidine 10 g (0.035 mole) 5,6-Dimethoxy-2-(pyridin-4-yl) methylene indan-1-one and 1 g Platinum dioxide were suspended in acetic acid-methanol mixture (200 ml:200 ml) at room temperature and 30 psi gauge for 6 hrs. Platinum dioxide was filtered off and the filtrate was concentrated. The residue was treated with 10% sodium hydrogen carbonate solution and the solution was extracted 3 times with methylenedichloride, dried and concentrated. Yield 10.1 g (99%). Corresponding HCl, mp 248–250° C., lit. mp 249–50° C., $^1$H NMR (base, 200 MHz CDCl$_3$) δ (ppm) 7.1 (s, 1H), 6.9 (s, 1H), 3.9 (s, 1H), 3.8 (s, 3H), 3.0–3.2 (m, 3H), 2.6–2.7 (m, 4H), 2.2 (bs, 1H, exchanges with D$_2$O), 1.6–1.7 (m, 4H), 1.2–1.3 (m, 3H).

EXAMPLE 2

1-benzyl-4-[(5,6-dimethoxy-1-indanon)-2-yl)methyl piperidine hydrochloride 10 g (0.0346 mol) of 4-[(5,6-dimethoxy-1-indanon)-2-yl] methyl piperidine was dissolved in 100 ml methylene dichloride followed by 6.5 g benzyl bromide and 13 g triethyl amine. The reaction mixture was refluxed for 4 hrs. The reaction mixture was filtered off and the filtrate was concentrated to yield 1-benzyl-4-[(5,6-dimethoxy-1-indanon)-2-yl]methyl piperidine free base which was redissolved in 100 ml methanol followed by addition of 10 ml methanolic—HCl (10%). The reaction mixture was cooled at 10° and the resulting solid was filtered and washed with cooled methanol.

Yield 13.16 g (92%). Mp 210–212°. $^1$H NMR (200 MHz CDCl$_3$) δ (ppm) 7.4 (m, 5H), 6.9 (s, 1H), 4.0 (s, 3H), 3.9 (s, 3H), 3.5 (s, 2H), 3.2 (dd, 1H), 2.9 (d, 2H), 2.7 (m, 2H), 2.0–1.4 (m, 9H). Overall yield 95.5% (99%×92%).

What is claimed is:

1. A process for the preparation of 1-benzyl-4-[(5,6-dimethoxy-1-indanon)-2-yl]methylpiperidine hydrochloride (Donepezil HCl) of the formula I

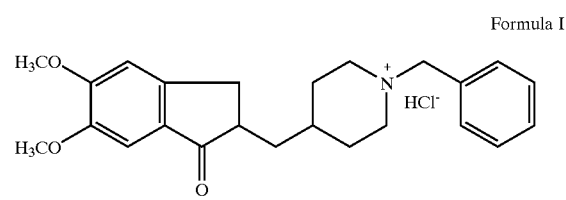

Formula I comprising hydrogenating 5,6-Dimethoxy-2-(pyridin-4-yl) methylene inda-1-one with a noble metal oxide catalyst in an organic solvent at 20–50° C. and 10–45 psi gauge pressure to form 4-[(5,6-dimethoxy-1-indanon)-2-yl]methyl piperidine of the formula II

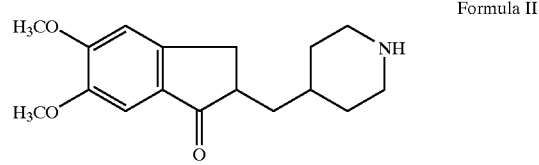

Formula II which is alkylated with an alkylating agent in an organic solvent at 20–80° C.

2. A process as claimed in claim 1, wherein the hydrogenation is carried out in acetic acid:methanol mixture.

3. A process as claimed in claim 1 wherein the hydrogenation is carried out with platinum dioxide catalyst.

4. A process as claimed in claim 1 wherein the hydrogenation is carried out at 25–40° C. and 25–40 psi gauge.

5. A process as claimed in claim 1, wherein the alkylation is carried out with benzyl bromide.

6. A process as claimed in claim 1, wherein the alkylation is carried out in methylene dichloride and triethyl amine mixture.

7. A process as claimed in claim 1, wherein the alkylation is carried out at 30–40° C.

* * * * *

UNITED STATES PATENT AND TRADEMARK OFFICE
CERTIFICATE OF CORRECTION

PATENT NO. : 6,649,765 B1 Page 1 of 1
DATED : November 18, 2003
INVENTOR(S) : Joshi Shreerang Vidyadhar et al.

It is certified that error appears in the above-identified patent and that said Letters Patent is hereby corrected as shown below:

<u>Title page, Item [54] and Column 1, line 4,</u>
Title -- HCI -- should be substituted for "HCL"

Signed and Sealed this

Second Day of March, 2004

JON W. DUDAS
*Acting Director of the United States Patent and Trademark Office*